United States Patent

Cooke

[11] 4,310,698
[45] Jan. 12, 1982

[54] FLUOROCHEMICAL NON-IONIC SURFACTANTS

[75] Inventor: Thomas W. Cooke, Mahopac, N.Y.

[73] Assignee: Ciba-Geigy Corporation, Ardsley, N.Y.

[21] Appl. No.: 166,275

[22] Filed: Jul. 7, 1980

Related U.S. Application Data

[63] Continuation of Ser. No. 953,296, Oct. 20, 1978, abandoned.

[51] Int. Cl.³ .................... C07C 149/18; C11D 1/722
[52] U.S. Cl. .................................. 568/46; 568/45; 252/174.22; 252/352
[58] Field of Search .................................. 568/45, 46

[56] References Cited

U.S. PATENT DOCUMENTS

| Re. 29,243 | 5/1977 | Umbach et al. | 568/46 |
|---|---|---|---|
| 3,081,354 | 3/1963 | Gaertner et al. | 568/46 |
| 3,700,646 | 10/1972 | Anello et al. | 568/45 |
| 3,758,595 | 9/1973 | Lamberti et al. | 568/46 |
| 3,821,372 | 6/1974 | Vanlerberghe et al. | 568/46 |
| 3,906,049 | 9/1975 | Hager et al. | 568/50 |
| 3,935,277 | 1/1976 | Dear et al. | 568/46 |

OTHER PUBLICATIONS

J. Moilliet et al., *Surface Activity*, pp. 442–443 (1961), Van Nostrand, Inc., NH.

*Primary Examiner*—Donald G. Daus
*Assistant Examiner*—D. Rivers
*Attorney, Agent, or Firm*—Michael W. Glynn

[57] ABSTRACT

Fluorochemical surfactants of the formula

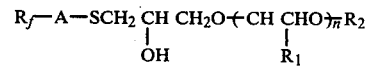

wherein $R_f$ is perfluoroalkyl of 4–20 carbon atoms or perfluoroalkoxyperfluoroalkyl of 4–20 carbon atoms;
A is straight or branched chain alkylene of 1–10 carbon atoms which is unsubstituted or substituted by halo;
n is 1 to 50;
$R_1$ is hydrogen or alkyl of 1–4 carbon atoms and $R_2$ is hydrogen or alkyl of 1–4 carbon atoms.

10 Claims, No Drawings

FLUOROCHEMICAL NON-IONIC SURFACTANTS

This is a continuation of application Ser. No. 953,296 filed on Oct. 20, 1978, now abandoned.

The instant invention relates to novel fluorinated non-ionic surfactants of the general formula

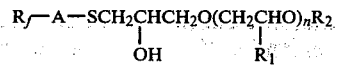

wherein
$R_f$ is perfluoroalkyl of 4 to 20 carbon atoms;
A is straight or branched chain alkyl of 1–10 carbon atoms which is unsubstituted or is substituted by chloro or fluoro;
n is 1–50
$R_1$ is hydrogen or alkyl of 1–4 carbon atoms and
$R_2$ is hydrogen or alkyl of 1–4 carbon atoms.

Preferably, $R_f$ is perfluoroalkyl of 4–16 carbon atoms or said perfluoroalkyl substituted by perfluoroalkoxy of 2–4 carbon atoms; A is ethylene; n is 5–25, $R_1$ is hydrogen and $R_2$ is hydrogen or methyl. Most preferably $R_2$ is methyl.

Where n is less than 5, the resulting compounds have little water solubility. However, such compounds are useful as surfactants in non-aqueous systems, as mold release agents in the plastics and silicone industry, as well as grease and oil repellants for paper. Those compounds wherein $R_1$ is predominately lower alkyl are likewise characterized by their limited water solubility and likewise possess utility as surfactants in non aqueous systems, as mold release agents and as grease and oil repellants for paper and the like.

Preferred compounds are those wherein $R_1$ is at least predominately hydrogen and n is 5–50. Such compounds are essentially water soluble.

Such water soluble compounds are valuable aqueous surfactants and are useful industrial wetting agents. Thus, they are useful wetting agents for biocides, cleaning compositions and detergents, as rinse-aids for cars, dishes and the like, as emulsifiers, and as leveling agents in the dye and pigment industry.

The compounds of the instant invention are easily prepared by any one of a number of routes.

For example. The compounds can be prepared conveniently by reacting a alkoxylated compound of the formula

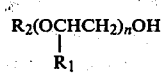

with epichlorohydrin in bulk or in a common dry and aprotic solvent, including ketones, such as acetone or methyl ethyl ketone; ethers, such as diethylether, ethylenegycol-dimethylether or tetrahydrofuran; esters such as ethyl acetate or methyl cellosolve acetate; and amides, such as dimethylformamide or N-methyl pyrrolidone. A Lewis acid catalyst, such as boron trifluoride (usually in the form of the diethyl ether complex thereof) or aluminum chloride, is used to promote the formation of the halohydrin intermediate. If the reaction is run in the absence of a solvent, it is advantageously run at a temperature above the melting point of the alkoxylated compound with boron trifluoride-etherate. The reaction is ordinarily exothermic. It is generally not necessary to isolate the halohydrin intermediate, and the next reaction can be carried out in the same reaction vessel. The halohydrin intermediate has the formula

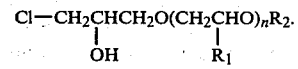

In the second step, the perfluoroalkylene mercaptan (R—A—SH) is added to the halohydrin intermediate, followed by the addition of an equivalent amount of base as an acid acceptor. This step may advantageously be carried out in bulk or in the presence of aprotic or protic solvents. As apotic solvents, there may be used those recited above for the first step. Suitable protic solvents include water, and alcohols such as methanol, ethanol, isopropanol, tert. butyl alcohol, hexyleneglycol and ethyleneglycol. Suitable bases include sodium hydroxide, potassium hydroxide, pyridine, lutidine and triethylamine. Conveniently, a solvent is selected which dissolves the reactants and desired product, but not the by-product salt, so that the salt will precipitate out as the reaction proceeds and can then be removed by conventional techniques, such as filtration. The fluorochemical surfactant product may be left in solution or evaporated to remove the solvent. The reaction is preferably carried out between about 30° and 80° C., under a nitrogen atmosphere, with stirring. There is generally an exotherm as the base is added to the reaction mixture.

Alternatively, the surfactants of the instant invention may be prepared by first reacting equimolar amounts of perfluoroalkylene mercaptan, $R_f$—A—SH, and epichlorohydrin by placing them in a reaction vessel and stirring the reactants in the presence of an inert solvent, such as methyl cellosolve acetate. Then a stoichiometric amount of a base, such as 50% aqueous sodium hydroxide, is slowly added to the reaction mixture. The resulting reaction is exothermic and the reaction temperature is advantageously maintained between about 20°–60° C. with stirring for B 1–3 hours. The resulting epoxide intermediate has the formula

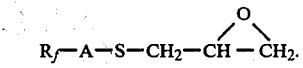

The by-product salt is removed from the epoxide intermediate and any residual water is removed by vacuum distillation.

The epoxide intermediate is then reacted with an equimolar amount, or a slight excess, of an alkoxylated compound of the formula

This reaction is advantageously conducted under substantially anhydrous conditions in the presence of a catalyst, such as $BF_3$. etherate, at a temperature of about 30°–60° C. in the presence or absence of an inert solvent, such as methyl cellosolve acetate. In one technique, the catalyst is dispersed in a mixture of the alkoxylated compound and the solvent, and slowly added to the epoxide intermediate with stirring. Preferably, this reaction is carried out under a nitrogen blanket.

The product fluorochemical surfactant may be left in solution and used as such, or may be evaporated or distilled under vacuum to remove the solvent.

The fluorochemical surfactants of this invention are distinguished by their increased surface active properties vis-a-vis their related hydrocarbon surfactant analogs. As a result, they improve or impart properties such as wetting, penetration, spreading, leveling, foam stability, flow properties dispersion properties and oil and water repellency.

The following Examples are set forth merely for purposes of illustration and do not limit the scope of the instant invention. All parts are by weight unless otherwise specified.

EXAMPLE 1

32.56 g (0.3520 moles) of epichlorohydrin was slowly added to a mixture of 140.0 g (0.4000 moles) Carbowax 350 (methoxypolyethoxy ethanol, MW≅350) and 1.60 g BF$_3$-diethyl etherate (47% BF$_3$) at a rate which maintained the exothermic reaction at 50°–60° C. After stirring for an additional ½ hour at 50°–60° C., 355.4 g of anhydrous isopropyl alcohol and 148.8 g (0.3200 moles) of perfluoroalkylethyl-mercaptan *(R$_f$CH$_2$CH$_2$SH, MW≅465) were added to the reaction vessel and stirred at ~50° C. Then 28.67 g (0.3584 moles) of 50% aq. sodium hydroxide was slowly added to the reaction mixture at a rate which maintained the exothermic reaction at 50°–60° C. A white precipitate formed (sodium chloride by-product) during the addition. The system was stirred for an additional 1 hour at 50°–55° C. After cooling to ~25° C., the resulting product mixture was filtered to remove the NaCl. 647 g of an amber solution were collected (at 94.3% yield of solution), containing the compound with the structure:

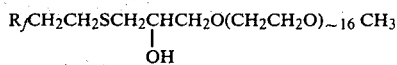

The product was an amber solution (43.2% solids found) which was soluble in water and toluene. 21.3% F found in solids (21.1% F calc.).

| Compound from | Measured Surface Properties in Deionized Water at 25° C. | | | | |
|---|---|---|---|---|---|
| | Measurement | Level of Actives | | | |
| | | 0.1% | 0.01% | 0.003% | 0.001% |
| Example 1 | surface tension (dynes/cm) | 21.0 | 22.3 | 32.9 | — |
| | interfacial tension (dynes/cm) | 12.1 | 17.2 | — | 24.3 |
| Example 2 | surface tension (dynes/cm) | 24.1 | 26.1 | 31.5 | 32.8 |
| | interfacial tension (dynes/cm) | 10.9 | 12.8 | — | 18.7 | note:
Interfacial tension measured against cyclohexane.

EXAMPLES 3–8

Using the procedure of Example 1, compounds of the general structure

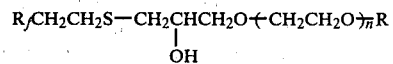

were prepared from the hydroxy compounds listed below, where "n" and "R" are defined in the table, and R$_f$≅1.7% C$_4$F$_9$, 32.9% C$_6$F$_{13}$, 36.4% C$_8$F$_{17}$, 21.8% C$_{10}$F$_{21}$, 5.4% C$_{12}$F$_{25}$, 0.6% C$_{14}$F$_{29}$.

| Example | Non-ionic Moiety | Value of "n" | Structure of "R" | Surface Tension, dynes/cm, in water | |
|---|---|---|---|---|---|
| | | | | at 0.1% actives | at 0.1% F |
| 3 | methyl Cellosolve | 1 | —CH$_3$ | not soluble | not soluble |
| 4 | methoxytriglycol | 3 | —CH$_3$ | slightly sol. | slightyl sol. |
| 5 | Carbowax 550 | ~12 | —CH$_3$ | 22.0 | 22.2 |
| 6 | Pluronic L-42 | ~9 | —(i-PrO)~$_{21}$H | 22.7 | 22.6 |
| 7 | Pluronic P-65 | ~38 | —(i-PrO)~$_{30}$H | 30.0 | 29.3 |
| 8 | butyl Cellosolve | 1 | —C$_4$H$_9$ | not soluble | not soluble |

*R$_f$=0.9% C$_4$F$_9$, 32.9% C$_6$F$_{13}$, 37.5% C$_8$F$_{17}$, 22.9% C$_{10}$F$_{21}$, 5.3% C$_{12}$F$_{15}$

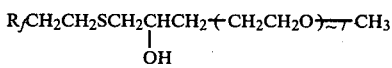

This product was slightly soluble in water and soluble in toluene. A portion of the solution was evaporated to solids (43.5% solids found) leaving an amber oil. 33.0% F found (32.1% F calc.)

EXAMPLE 2

In the same manner as Example 1, 24.42 g (0.2640 moles) of epichlorohydrin, 225.0 g (0.3000 moles) of Carbowax 750 (methoxypolyethoxy ethanol, MW≅750), 1.60 g BF$_3$-diethyl etherate, 412.2 g anhydrous isopropyl alcohol, 111.6 g (0.2400 moles) of perfluoroalkylethyl mercaptan (same R$_f$-distribution as in Example 1), and 21.50 g (0.2688 moles) of 50% aq. sodium hydroxide were utilized to prepare 742 g (95.0% yield) of a solution containing the compound:

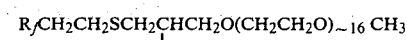

EXAMPLE 9

By the process of Example 1, 4.1 g (0.044 moles) of epichlorohydrin, 95.0 g (0.05 moles) of Carbowax 2000 (methoxypolyethylene glycol, MW≅1900), 0.3 g BF$_3$-ether complex, 146.3 g ann. isopropyl alcohol, 23.6 g (0.04 moles) of perfluoroalkylethyl mercaptan (MW≅588.8, see R$_f$-distribution below), and 3.6 g (0.0448 moles) of 50% sodium hydroxide were used to prepare the compound:

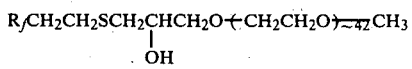

where R$_f$=0.5% C$_6$F$_{13}$, 24.1% C$_8$F$_{17}$, 48.1% C$_{10}$F$_{21}$, 21.7% C$_{12}$F$_{25}$, 2.8% C$_{14}$F$_{29}$.

234.6 g of a thick white suspension (at room temperature) were obtained at 42.9% solids, found. The solids were a white hard wax.

| Surface Tension Results: | 31.5 dynes/cm at 0.1% actives |
| --- | --- |
| | 48.1 dynes/cm at 0.01% actives |
| | 61.3 dynes/cm at 0.001% actives |

EXAMPLE 10

Also by the process described in Example 1, 6.48 g (0.07 moles) of epichlorohydrin, 5.33 g (0.07 moles) of 2-methoxyethanol, 0.1 g of BF$_3$-ether complex, 5-.6 g of ann. isopropyl alcohol, 33.72 g (0.07 moles) of perfluorooctylethyl mercaptan ($C_8F_{17}CH_2$ $CH_2$ SH), and 5.60 g of 50% sodium hydroxide were used to prepare 37.4 g of isolated solids (87% yield) of the following compound:

$$C_8F_{17}CH_2CH_2SCH_2\underset{\underset{OH}{|}}{C}HCH_2OCH_2CH_2OCH_3$$

calculated: 31.38% C; 2.80% H; 52.74% F. found: 30.43% C; 2.51% H; 52.99% F.

EXAMPLE 11

By the process of Example 1, 2.31 g (0.025 moles) epichlorohydrin, 18.75 g (0.025 moles) of Carbowax MPEG 750 (Union Carbide Corp.), 0.1 g BF$_3$-ether complex, 35.22 g ann. isopropyl alcohol, 8.65 g (0.025 moles) of $(CF_3)_3CFOCH_2CH_2CH_2CH_2$ SH, and 2.00 g (0.25 moles) of 50% sodium hydroxide were used to prepare the compound:

$$(CF_3)_2CFOCF_2CF_2CH_2CH_2SCH_2\underset{\underset{OH}{|}}{C}HCH_2O(CH_2CH_2O)_{\overline{n=16}}CH_3$$

The product (evaporated to solids) was a yellow wax.
Surface Tension = 18.0 dynes/cm at 0.1% in deion. water
Calculated: 45.3% C; 6.8% H; 18.4% F. Found: 45.5% C; 7.1% H; 15.6% F.

EXAMPLE 12-13

The following compounds were made in the same manner as Example 1, with the exception that Cellosolve was used in the second step of the reaction as the solvent. The amount of Cellosolve used was twice the amount of solids present.

$$R_fCH_2CH_2S-CH_2\underset{\underset{OH}{|}}{C}HCH_2O(CH_2CH_2O)_{\overline{n}}R$$

In the Table below, the R$_f$ distribution of A is 33.0% $C_6F_{13}$, 37.5% $C_8F_{17}$, 23.0% $C_{10}F_{21}$, 5.3% $C_{12}F_{23}$ and 0.2% $C_{14}F_{29}$ (balance=inerts); B is 5.5% $C_6F_{13}$, 40.8% $C_8F_{17}$, 39.2% $C_{10}F_{21}$, 11.0% $C_{12}F_{25}$ and 1.1% $C_{14}F_{29}$ (balance=inerts); and C is 1.0% $C_6F_{13}$, 15.9% $C_8F_{17}$, 59.0% $C_{10}F_{21}$, 17.4 $C_{12}F_{25}$ and 2.2% $C_{14}F_{29}$ (balance=inerts).

| | | | | | Surface tension Deion. Water-Dynes/Cm. | | | Appearance of dilution in Water 1-2% |
| --- | --- | --- | --- | --- | --- | --- | --- | --- |
| Ex. | Prepared from | n | R | R$_f$ | at 0.1% | 0.01% | 0.001% | solids |
| 12 | Carbowax 350 | ~7 | CH$_3$ | A | 20.0 | 21.8 | 37.1 | hazy |
| 13 | Carbowax 350 | ~7 | CH$_3$ | A | 19.8 | 22.1 | 36.1 | hazy |
| 14 | Carbowax 550 | ~12 | CH$_3$ | A | 22.3 | 24.1 | 39.7 | clear |
| 15 | Carb. 350 550 (50/50 blend) | ~7-12 | CH$_3$ | A | 21.6 | 23.0 | 40.0 | clear |
| 16 | Carbowax 750 | ~16 | CH$_3$ | A | 24.0 | 28.9 | 44.7 | clear |
| 17 | Carbowax 750 | ~16 | CH$_3$ | B | 24.5 | 29.8 | 44.2 | sl. hazy |
| 18 | Carbowax 750 | ~16 | CH$_3$ | C | 24.0 | 30.0 | 54.6 | hazy |

What is claimed is:

1. A fluorochemical surfactant of the formula $$R_f-A-S-CH_2\underset{\underset{OH}{|}}{C}HCH_2O(CH_2\underset{\underset{R_1}{|}}{C}HO)_{\overline{n}}R_2$$

wherein
R$_f$ is perfluoroalkyl of 4-20 carbon atoms or perfluoroalkoxyperfluoroalkyl of 4-20 carbon atoms;
A is straight or branched chain alkylene of 1-10 carbon atoms which is unsubstituted or substituted by halo;
n is 1-50;
R$_1$ is hydrogen or alkyl of 1-4 carbon atoms; and
R$_2$ is hydrogan or alkyl of 1-4 carbon atoms.

2. A fluorochemical surfactant according to claim 1, wherein R$_f$ is perfluoroalkyl of 4-20 carbon atoms and A is unsubstituted alkylene of 1-4 carbon atoms.

3. A fluorochemical surfactant according to claim 2, wherein R$_1$ is hydrogen and R$_2$ is alkyl of 1-4 carbon atoms.

4. A fluorochemical surfactant according to claim 3, wherein n is 5-25.

5. A fluorochemical surfactant according to claim 4, wherein R$_2$ is methyl and A is ethylene.

6. A fluorochemical surfactant according to claim 2, wherein R$_1$ is alkyl of 1-4 carbon atoms and R$_2$ is hydrogen.

7. A fluorochemical surfactant according to claim 6, wherein R$_1$ is methyl.

8. A fluorochemical surfactant according to claim 7, wherein n is 5-25.

9. A fluorochemical surfactant according to claim 1, wherein R$_2$ is alkyl of 1-4 carbon atoms and A is ethylene.

10. A fluorochemical surfactant according to claim 9, wherein R$_2$ is methyl and R$_1$ is hydrogen.

* * * * *